(12) United States Patent
Chowdhary et al.

(10) Patent No.: US 10,145,707 B2
(45) Date of Patent: Dec. 4, 2018

(54) HIERARCHICAL CONTEXT DETECTION METHOD TO DETERMINE LOCATION OF A MOBILE DEVICE ON A PERSON'S BODY

(75) Inventors: Mahesh Chowdhary, San Jose, CA (US); Manish Sharma, Noida (IN); Arun Kumar, New Delhi (IN); Anuraag Gupta, New Delhi (IN); Prateek Agrawal, Dehradun (IN)

(73) Assignee: CSR Technology Holdings Inc., San Diego, CA (US)

( * ) Notice: Subject to any disclaimer, the term of this patent is extended or adjusted under 35 U.S.C. 154(b) by 382 days.

(21) Appl. No.: 13/115,940

(22) Filed: May 25, 2011

(65) Prior Publication Data

US 2012/0303271 A1 Nov. 29, 2012

(51) Int. Cl.
*G01C 21/00* (2006.01)
*G01C 22/00* (2006.01)
(Continued)

(52) U.S. Cl.
CPC .......... *G01C 22/006* (2013.01); *A61B 5/0022* (2013.01); *A61B 5/1112* (2013.01); *A61B 5/1123* (2013.01); *A61B 5/6801* (2013.01); *A61B 5/7242* (2013.01); *G01C 21/16* (2013.01); *A61B 2562/0219* (2013.01); *G06F 19/00* (2013.01); *G16H 40/67* (2018.01)

(58) Field of Classification Search
CPC .... G01C 21/16; G01C 22/006; A61B 5/0022; A61B 5/1112; A61B 5/1123; A61B 5/6801; A61B 5/7242
USPC ....... 701/400, 408, 433, 468–472, 491, 500, 701/526, 541; 340/539.1, 593.13, 545.2, 340/545.5, 539.13
See application file for complete search history.

(56) References Cited

U.S. PATENT DOCUMENTS 6,132,391 A * 10/2000 Onari ................. G01C 21/005
600/595
6,253,172 B1 * 6/2001 Ding et al. .................... 704/219
(Continued)

FOREIGN PATENT DOCUMENTS

| CN | 101427570 A | 5/2009 | |
| DE | 102010031350 A1 * | 1/2012 | ............. G01C 21/04 |
| WO | WO2010/134010 | 11/2010 | |

OTHER PUBLICATIONS

Chetry et al. "Linear Predictive Models for Musical Instrument Identification" Acoustics, Speech and Signal Processing 2006. ICASSP 2006 Proceedings. 2006 IEEE International Conference on May 14-19, 2006; vol. 5; p. V.*

(Continued)

*Primary Examiner* — Chuong P Nguyen
(74) *Attorney, Agent, or Firm* — Thien T. Nguyen

(57) ABSTRACT

The present invention is related to detecting location of a navigation device using sensor data analysis, where the sensor is coupled to the navigation device. A hierarchical algorithm is used for making a series of decisions regarding the location of the navigation device, with each decision corresponding to a class among a plurality of classes related to the possible motion modes and/or precise location of the device, including the location of the device with respect to a person's body. By accurately identifying the device location, the hierarchical algorithm facilitates in providing relevant contextual information, thereby enhancing situational awareness.

17 Claims, 8 Drawing Sheets

(51) Int. Cl.
*A61B 5/00* (2006.01)
*A61B 5/11* (2006.01)
*G01C 21/16* (2006.01)
*G06F 19/00* (2018.01)
*G16H 40/67* (2018.01)

(56) References Cited

U.S. PATENT DOCUMENTS

| | | | | |
|---|---|---|---|---|
| 6,522,266 | B1* | 2/2003 | Soehren | A61B 5/7264 340/988 |
| 6,590,536 | B1* | 7/2003 | Walton | 342/463 |
| 7,103,471 | B2* | 9/2006 | Levi | A61B 5/1116 235/105 |
| 7,334,472 | B2* | 2/2008 | Seo et al. | 73/379.01 |
| 7,421,369 | B2* | 9/2008 | Clarkson | 702/150 |
| 7,610,166 | B1* | 10/2009 | Solinsky | G01C 21/005 702/141 |
| 7,811,203 | B2* | 10/2010 | Unuma et al. | 482/8 |
| 7,905,815 | B2* | 3/2011 | Ellis et al. | 482/8 |
| 8,775,128 | B2* | 7/2014 | Meduna | G06F 17/00 702/179 |
| 2006/0284979 | A1 | 12/2006 | Clarkson | |
| 2007/0233473 | A1* | 10/2007 | Lee et al. | 704/219 |
| 2007/0260418 | A1* | 11/2007 | Ladetto et al. | 702/150 |
| 2008/0214360 | A1 | 9/2008 | Stirling et al. | |
| 2009/0138200 | A1* | 5/2009 | Hunter et al. | 701/216 |
| 2009/0254279 | A1 | 10/2009 | Han et al. | |
| 2010/0171628 | A1* | 7/2010 | Stansfield | 340/669 |
| 2010/0321246 | A1* | 12/2010 | Troesken et al. | 342/463 |
| 2011/0029277 | A1 | 2/2011 | Chowdhary et al. | |
| 2011/0106449 | A1 | 5/2011 | Chowdhary et al. | |
| 2011/0248704 | A1 | 10/2011 | Chowdhary et al. | |
| 2012/0004881 | A1* | 1/2012 | Jung et al. | 702/141 |
| 2012/0265716 | A1* | 10/2012 | Hunzinger | G06K 9/00 706/12 |
| 2013/0245986 | A1* | 9/2013 | Grokop et al. | 702/141 |
| 2015/0153380 | A1* | 6/2015 | Elhoushi | G01P 15/14 702/141 |
| 2016/0206921 | A1* | 7/2016 | Szabados | A61B 5/0024 |
| 2018/0001174 | A1* | 1/2018 | Aoshima | A61B 5/02444 |

OTHER PUBLICATIONS

Search Report dated Sep. 14, 2012 in EP12169366.
Xiaoji Niu et al., U.S. Appl. No. 12/471,147, filed May 22, 2009.

* cited by examiner

HIERARCHICAL CONTEXT DETECTION METHOD TO DETERMINE LOCATION OF A MOBILE DEVICE ON A PERSON'S BODY

FIELD OF THE INVENTION

The present invention is related to location detection systems, and more particularly, to a method and apparatus of hierarchically detecting and using motion information in a mobile device.

BACKGROUND OF THE INVENTION

With the development of radio and space technologies, several satellites based navigation systems (i.e. satellite positioning system or "SPS") have already been built and more will be in use in the near future. SPS receivers, such as, for example, receivers using the Global Positioning System ("GPS", also known as NAVSTAR, have become commonplace. Other examples of SPS systems include, but are not limited to, the United State ("U.S.") Navy Navigation Satellite System ("NNSS") (also known as TRANSIT), LORAN, Shoran, Decca, TACAN, NAVSTAR, the Russian counterpart to NAVSTAR known as the Global Navigation Satellite System ("GLONASS") and any future Western European SPS such as the proposed "Galileo" program. As an example, the U.S. NAVSTAR GPS system is described in GPS Theory and Practice, Fifth ed., revised edition by Hofmann-Wellenhof, Lichtenegger and Collins, Springer-Verlag Wien New York, 2001, which is fully incorporated herein by reference.

The U.S. GPS system was built and is operated by the United States Department of Defense. The system uses twenty-four or more satellites orbiting the earth at an altitude of about 11,000 miles with a period of about twelve hours. These satellites are placed in six different orbits such that at any time a minimum of six satellites are visible at any location on the surface of the earth except in the polar region. Each satellite transmits a time and position signal referenced to an atomic clock. A typical GPS receiver locks onto this signal and extracts the data contained in it. Using signals from a sufficient number of satellites, a GPS receiver can calculate its position, velocity, altitude, and time (i.e. navigation solution).

GPS and other satellite based navigational systems have some limitations such as dependence on the availability of a sufficient number of satellite signals, and/or dependence on strength of the available signals. Satellite signals are sometimes not available in deep canyon-like geographical environments, e.g., in areas with large number of tall buildings blocking the direct satellite signals, in dense forest areas, etc. In addition to this, the satellite signals can be completely blocked or greatly attenuated inside buildings, or at underground locations, such us subway stations in a metropolitan area, basement of a house/commercial building etc. Additionally, weak satellite signal may be corrupted by other stronger signals naturally or intentionally.

To reduce these errors, inertial measurement units (IMUs) equipped with sensors can be integrated with a navigation device to provide data that is used to improve the position predictability and reliability of the device in degraded signal environments. For example, in an indoor environment where satellite signals are not available or in a dense urban environment where multipath errors are common, sensor data can aid in the calculation of a navigation solution. Typical IMUs include gyroscopes that measure changes in direction, accelerometers that estimate acceleration, magnetic sensors that can detect changes in the orientation of a device, and a host of other similar devices. More particularly, after the position of a navigation device is initially determined, the IMUs allow the position of the navigation device to be determined as the navigation device moves, even if the satellite signals are blocked.

The determination of a position by propagating a previous known position based on movement data (e.g., data provided by an IMU) can be used is inertial navigation, such as a dead-reckoning (DR) method. DR methods do not typically take into account contextual information regarding how the navigation device is moving. Co-pending co-owned U.S. application Ser. No. 12/510,965, published as U.S. Publication No. 2011/0029277, titled, "Methods and Applications for Motion Mode Detection for Personal Navigation Systems," advanced the state of the art by disclosing methods and apparatuses for detecting and using motion modes in a personal navigation device.

However, there is room for improvement in the use of motion data of a navigation device to enhance user experience by more accurately pinpointing a navigation device's location, and associating contextual/situational information with the user based on the device's detected location. For example, current methods are not optimized for precisely predicting the position of the navigation device on a person's body. Moreover, position detection algorithms are not optimized to exploit the inherent hierarchy in collected locational data obtained from the sensors.

SUMMARY OF THE INVENTION

The present invention is related to detecting location of a navigation device by analyzing sensor data, for example one or more motion sensors coupled to the navigation device. A hierarchical algorithm uses the sensor data for making a series of decisions regarding the location of the navigation device, with each decision corresponding to a class among a plurality of classes related to the possible motion modes and/or precise location of the device, including the location of the device with respect to a person's body. By accurately identifying the device location, the hierarchical algorithm facilitates in providing relevant contextual information, thereby enhancing situational awareness for the user.

In the present disclosure, the term "personal navigation device" (PND) is used as a non-limiting illustrative example of a portable navigation device. The navigation device may be a standalone navigation device, or may be a navigation module coupled to other portable devices, such as a mobile phone, a laptop/notebook/tablet computer, a personal digital assistant (PDA), a portable entertainment console (such as mobile TV, iphone, ipad etc.), a portable electronic reader device, a watch, a portable digital gaming console, a portable picture taking/editing device (e.g. a camera), a cosmetic accessory (e.g., a pendant) etc. Broadly defined, a PND enhances the user experience by autonomously or semi-autonomously determining accurate locational information, and other contextual information associated with that detected location and motion.

The locational information can be provided with a predefined acceptable level of accuracy based on an intelligent algorithm even in environments where a GPS signal is absent or otherwise weakened or compromised, such as, in a deep indoor environment, in an urban canyon, at an underground train station, etc. Additionally, the algorithm is largely independent of traditional location aiding services typically provided by existing infrastructure, such as an assisted-GPS infrastructure, where a GPS signal is absent or non-optimal.

According to an aspect of this invention, a method for determining position information about a device is disclosed, the method comprising: performing a first level of classification to detect a motion mode of the device by distilling data collected from one or more sensors coupled to the device; and, performing a second level of classification to detect a location of the device on a user's body by further distilling data collected from the one or more sensors.

According to another aspect of the invention, a location positioning apparatus for a device is disclosed, comprising: an input coupled to receive data from an inertial motion unit (IMU) of the device; a processor that determines, based on a first level of classification using the received data, the current motion mode of the mobile device to be a particular motion mode in a plurality of motion mode, and further determines, based on a second level of classification using the received data, the current location of the device with respect to a user's body.

These and other aspects of the present invention, including systems and computer program products corresponding to the above methods, will be apparent to a person skilled in the art in view of the following drawings and detailed description.

BRIEF DESCRIPTION OF THE DRAWINGS

Aspects and features of the present invention will become apparent to those ordinarily skilled in the art upon review of the following description of specific embodiments of the invention in conjunction with the accompanying figures, wherein.

DETAILED DESCRIPTION OF THE PREFERRED EMBODIMENTS

The present invention will now be described in detail with reference to the drawings, which are provided as illustrative examples of the invention so as to enable those skilled in the art to practice the invention. Notably, the figures and examples below are not meant to limit the scope of the present invention to a single embodiment, but other embodiments are possible by way of interchange of some or all of the described or illustrated elements. Moreover, where certain elements of the present invention can be partially or fully implemented using known components, only those portions of such known components that are necessary for an understanding of the present invention will be described, and detailed descriptions of other portions of such known components will be omitted so as not to obscure the invention. Embodiments described as being implemented in software should not be limited thereto, but can include embodiments implemented in hardware, or combinations of software and hardware, and vice-versa, as will be apparent to those skilled in the art, unless otherwise specified herein. In the present specification, an embodiment showing a singular component should not be considered limiting, rather, the invention is intended to encompass other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

Figure 1:
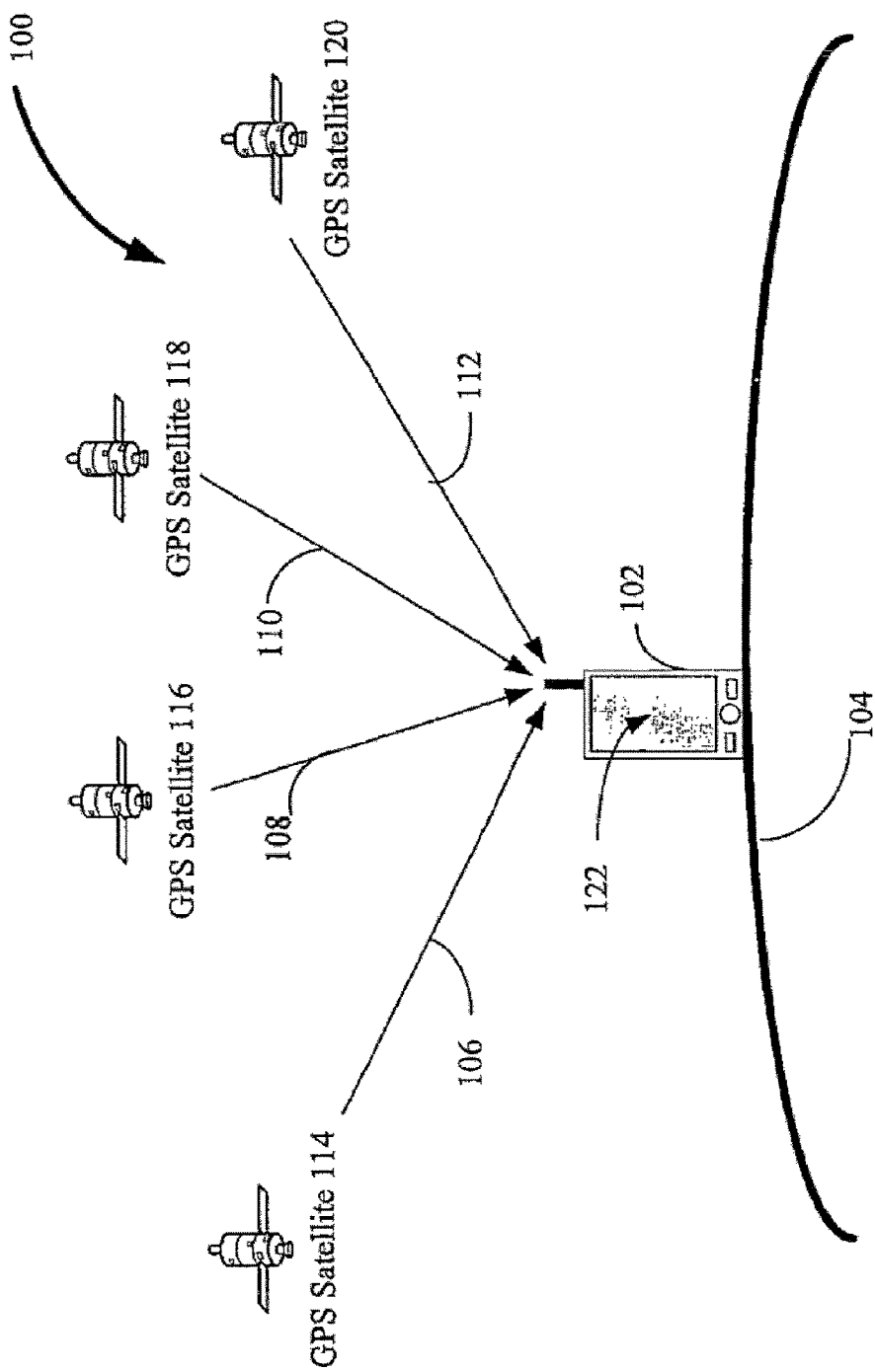
FIG. 1 is a diagram of an example implementation of principles of the invention.

FIG. 1 illustrates an example implementation of a satellite-based communication system. As shown in FIG. 1, GPS satellites (i.e. SVs) 114, 116, 118 and 120 broadcast signals 106, 108, 110 and 112, respectively, that are received by GPS device 102, which is located at a user position somewhere relatively near the surface 104 of earth.

GPS device 102 can be a handheld/portable personal navigation device (PND, e.g., PNDs available from Garmin, TomTom, etc.) or a cell phone, iPhone, PDA, handheld or laptop computer, or other type of device with built-in GPS functionality, or any GPS device embedded in tracking applications (e.g., automotive tracking from Trimble, package or fleet management tracking from FedEx, child locator tracking applications, etc.). Such GPS functionality can be implemented by chipsets such as SiRFStarV and other chipsets from CSR/SiRF Technology, Inc., for example, which include core processors and embedded storage and software for processing received GPS/SPS signals and/or determining a navigation solution based on the received and processed signals.

As will become more apparent from the descriptions below, GPS device 102 according to aspects of the invention also includes sensors such as accelerometers, pressure sensors, gyroscopes and the like (collectively, inertial measurement unit or IMU). GPS device 102 may also include DR functionality, as adapted with the functionality of the present invention. Example sensors and functionality that can be adapted for use in the present invention are described in more detail in co-pending application Ser. Nos. 11/823,964 (now published as U.S. Publication No. 2009/0254279) and 12/471,147, commonly owned by the present assignee, the contents of which are incorporated by reference herein in their entirety. Those skilled in the art will be able to understand how to adapt the apparatuses and functionality depicted in those applications for use with the techniques of the present invention, and so further details thereof will be omitted here for sake of clarity of the invention.

Signals 106, 108, 110 and 112 are well-known GPS signals in which three binary codes shift the satellite's transmitted L1 and/or L2 frequency carrier phase. As is known, signals from at least four SVs are usually needed before device 102 can provide a 3-dimensional navigation solution (only three satellites are required for a 2-dimensional navigation solution; e.g., by using known altitude).

As described before, the present invention uses a hierarchical algorithm to broadly detect a motion mode of a navigation device (e.g., whether a person carrying the device is walking, is in a vehicle, is jogging, or is stationary, etc.), and additional finer-level of information regarding the physical location of a navigation device (e.g., on the person's body, within/coupled to an item of clothing, or within/coupled to a carrier, such as a bag, etc.). Inherently, the nature of the locational data associated with the PND is hierarchical, therefore the collected sensor data, e.g. data collected from one or more IMUs coupled to the PND, is also hierarchical. The locational information is gleaned efficiently by exploiting existing hierarchy in collected sensor data. In other words, the hierarchical algorithm in some embodiments described herein creates a predefined contextual classification framework in which collected sensor data can be fed (automatically or semi-automatically) and analyzed, such that the output of the algorithm is indicative of the location of the navigation device with a certain confidence level. The algorithm is preferably flexible enough to choose the classifiers, including time-domain and/or frequency-domain classifiers. At the same time, due to the hierarchical nature, the algorithm is faster than alternative non-hierarchical generic diagnosis/detection algorithms that do not take advantage of the fact that the collected sensor data is naturally segmented into clusters, i.e. naturally hierarchical. One of the features of the present invention is the ability to recognize the natural segmentation of the collected sensor data, and associate a proper classifier to each segment of data, as will be elaborated further with illustrative examples.

As described before, an aspect of the present invention is to accurately determine a device location. Device location may also be associated with detection of motion mode and/or finer-level of positional information about the device with respect to a person's body. A motion mode indicates whether and/or how the PND is moving. Since a PND is typically carried by a human user, examples of motion modes include: stationary, walking, fast walking, jogging, climbing up/down stairs, going up/down on an escalator, going up/down on an elevator, biking, driving, riding in a vehicle such as a car, bus, boat, airplane, etc.

The motion modes/device locations determined may be used in a variety of applications, including improving the situation awareness of a user, even in environments where GPS navigation signal is absent or minimal. A motion mode/device location may be used to select an appropriate position determination algorithm for DR purposes, thereby increasing the accuracy of the positions computed by the DR algorithm. For example, when a user carrying a PND drives into a parking garage and begins to walk into an indoor environment, satellite signals will become unavailable and DR algorithms must be relied on to continue to produce position estimates. With a motion mode available, an appropriate DR algorithm (e.g., one catered to pedestrian walking, known as Pedestrian Dead Reckoning or PDR) may be selected to produce better position estimates. The motion mode classification may change from "driving" to "walking" upon detection, using the methods discussed below, upon the user's stopping the car and commencement of walking. In addition, waypoints for the walking session may be continuously stored so that when the user desires to return to the location of the parked vehicle, the waypoints can be used to guide the user back.

In another embodiment, motion mode detection may be used to improve PDR algorithms. Pedestrian algorithms may have four example components: (1) step detection; (2) stride length estimation; (3) heading determination; and (4) sensor calibration. The sensors are calibrated when the PND is detected to be stationary. For example, accelerometers, gyroscopes, magnetic sensors, and pressure sensors all exhibit drift in bias and sensitivity that is dependent on time, temperature or other environmental factors. The bias for these sensors can be reset upon detection of a stationary condition. In other words, one of the applications of the present inventions includes keeping track of and possibly compensating for drift-error build-up.

In another embodiment, the detection of a stationary state is used to constrain location uncertainty growth. Indoor position computation routines that rely on pedestrian DR, WiFi triangulation, and Receiver Signal Strength Indicator (RSSI) methods all have uncertainty variations that are dependent on the period of time since the last good position fix. With detection of a stationary state, the period of time since the last good position fix does not need to increase, resulting in extended availability of location solution with a desired level of accuracy lasting for a longer period of time. As a result, the uncertainty growth in computation of location is constrained.

In another embodiment, the detection of a stationary state is used to determine when to power off the PND, resulting in significant power savings.

Yet another example may be associated with turning on/off an 'airplane mode.' Once an 'airplane mode' is turned on, the PND stops trying to determine real time position. Instead, if the relevant information about the destination of the airplane is provided by the user or is automatically detected by the device at the starting point, then once the airplane mode is turned off, the PND may instantly display the locational information at the destination.

The above example applications have significant commercial advantages both from vendors' and the user/consumers' perspectives. For example, when a user is inside a subway station, he can still get situational information about train services and/or other commercial services (e.g. location of restaurants, location of Automated Teller Machines, etc.). In another example, if a user is roaming inside a department store, where GPS signal is low/blocked, the hierarchical algorithm may still be able to navigate the user to a particular item that he is looking for. From the store owner's perspective, detecting the user's location may be helpful in: 1) sending generic product information (and/or coupons) to the user's PND based on the user's proximity to a certain product, 2) sending personalized product information (or coupons) to the user's PND based on the user's likelihood of buying a certain product as determined from his personal profile and/or historical purchase records in the same/different store; 3) guiding the user to a product that he is looking for, etc.

Typically, in many of the above example scenarios, an existing infrastructure of location-aiding services, such as assisted GPS infrastructure is used. However, the hierarchical algorithm disclosed herein has the potential of intelligently choosing a classification system, where locational information can be derived without relying on (or minimally relying on) an existing location-aiding infrastructure. In other words, the hierarchical method is largely agnostic of and operationally independent of the infrastructure that it is physically adjacent to.

In all of the position detection methods discussed here, first movement data is collected from the IMU of the PND device. This movement data may be, for example, acceleration data from an accelerometer. Additionally or alternatively, the movement data may be angular rate from a gyroscope, altitude variation data from a pressure sensor, or heading, pitch, and roll angles from a combination of magnetic sensor and accelerometer.

Persons skilled in the art will recognize that IMUs may be equipped with a variety of sensors, including micro-electromechanical-systems (MEMS)-based sensors with miniaturized moving parts. Types of example MEMS sensors may include magnetic field sensors, pressure sensors, accelerometers, gyroscopes etc. Sensors are not limited to moving-parts-based MEMS technology only. For example, Hall-effect-based magnetic field sensors may be designed and characterized without any miniature moving part.

Often multiple sensors may be coupled to a PND. In that case, multi-sensor data fusion/data segregation to fit the hierarchical algorithm framework becomes relevant. In other words, sensor characterization and/or quantitative calibration are closely related to hierarchical decision making and context detection concept discussed herein.

As briefly mentioned before, the present invention utilizes a hierarchical-algorithm based classification, that can be done in frequency-domain and/or time-domain, or utilizing a combination of frequency-domain and time-domain analyses. Co-pending co-owned U.S. application Ser. No. 12/510,965, now published as U.S. Publication No. 2011/0029277, titled, "Methods and Applications for Motion Mode Detection for Personal Navigation Systems," describes frequency-domain motion mode detection methods. Embodiments of the present invention include and extend the methods into time-domain analysis as well.

In a frequency-domain method of motion mode detection, first the movement data from an IMU of the PND device is collected. Next, linear prediction coefficients (LPC) are generated for the collected movement data. Frequency-domain classification can be based on changes in movement such as stride length or stride rate. One motivation behind this is that short sequences of accelerometer/gyroscope (or other sensor) data can be assumed to be stationary, thus enabling modeling of the data as the output of a Finite Impulse Response (FIR) filter driven by zero mean white noise. Such a filter's transfer function is essentially an Autoregressive (AR) model.

A periodic signal, such as the movement data collected by an IMU unit that represents near-periodic signals such as walking, fast walking, jogging, etc., can be approximated by a linear combination of the signal's past p sample values.

$$x(n) = a_1 x(n-1) + a_2 x(n-2) + \ldots + a_p x(n-p) + e(n)$$

$$= \sum_{1}^{i=p} a_i x(n-i)$$

where the coefficients $a_1, a_2, \ldots, a_p$ are the linear prediction coefficients (LPC). A linear predictor with prediction coefficients $b_k$ is a prediction system whose output $X(n)$, is an estimation of the data $x(n)$. $X(n)$ is estimated based on previous values of $x$ (e.g., $x(n-1)$, $x(n-2)$, etc.). The linear predictor may be an autoregressive (AR) model.

$$X(n) = b_1 X(n-1) + b_2 X(n-2) + \ldots + b_p X(n-p)$$

$$= \sum_{1}^{k=p} b_k X(n-k)$$

The prediction error, $e(n)$, is the approximation error at time n, and is the difference between $x(n)$ and $X(n)$:

$$e(n) = x(n) - X(n)$$

By minimizing the square sum of the prediction error, a unique set of linear-prediction coefficients (LPC) may be obtained. For example, using this technique, one can get the correct value of motion parameter required to generate/reconstruct the motion, such as human walking, running etc. Also, once the order of the AR model has been determined, the AR coefficients $a_1, a_2, \ldots, a_p$ may be estimated by an auto-correlation method known as the Yule-Walker equations:

$$\begin{bmatrix} r_x(0) & r_x(1) & \ldots & r_x(p) \\ r_x(1) & r_x(0) & \ldots & r_x(p-1) \\ r_x(2) & r_x(1) & \ldots & r_x(p-2) \\ \ldots & \ldots & \ldots & \ldots \\ r_x(p) & r_x(p-1) & \ldots & r_x(0) \end{bmatrix} \begin{bmatrix} 1 \\ a_1 \\ a_2 \\ \ldots \\ a_p \end{bmatrix} = \begin{bmatrix} \sigma^2 \\ 0 \\ 0 \\ \ldots \\ 0 \end{bmatrix}$$

where $$r_x(k) = \sum_{n=0}^{n-1-k} X(n) X(n+k)$$

In the frequency domain, the transfer function of the AR model is:

$$H(z) = \frac{G}{1 - \sum_{k=1}^{p} b_k z^{-1}}$$

Based on this transfer function, the LPC may be converted into line spectral frequencies (LSF) as follows. First, H(z) may be represented as the sum of an even symmetric and an odd symmetric filter, P(z) and Q(z), such that:

$$H(z) = \frac{P(z) + Q(z)}{2}$$

where $$P(z) = 1 - (a_1 + a_N)z^{-1} - \ldots - (a_1 + a_N)z^{-N} + z^{-(N+1)}$$

$$Q(z) = 1 - (a_1 - a_N)z^{-1} - \ldots - (a_1 - a_N)z^{-N} + z^{-(N+1)}$$

P(z) and Q(z) have roots at z=1 and z=−1, respectively, so P(z) and Q(z) can be written as:

$$P'(z) = \frac{P(z)}{(1+z)} = (p_0)z^N + (p_1)z^{N-1} + \ldots + (p_k)z^{N-k} + \ldots (p_N)$$

$$Q'(z) = \frac{Q(z)}{(1-z)} = (q_0)z^N + (q_1)z^{N-1} + \ldots + (q_k)z^{N-k} + \ldots (q_N)$$

where $p_0 = 1, q_0 = 1$ $p_k = -(a_k + a_{N+k-1}) - p_{k-1}$ for $k = 1, 2, \ldots, N$ $q_k = (-a_k + a_{N+k-1}) + q_{k-1}$ for $k = 1, 2, \ldots, N$ The roots of the two equations immediately above are the line spectral frequencies (LSF).

Once the LSF is obtained, the LSF is compared to the LSF of previously obtained training motion data for the various motion modes and a spectral distortion ($D_{sp}$) value is computed for the LSF from the collected motion data and the training LSF for each of the various motion modes. The spectral distortion ($D_{sp}$) value is computed based on the following:

$$D_{sp} = \frac{1}{2\pi}\int_{-\pi}^{\pi}(10\log_{10}S(w) - 10\log_{10}S_t(w))^2\,dw$$

where S(w) is the spectral representation of the collected motion data and $S_t(w)$ is the spectral representation of training motion data for a particular motion mode.

Once the spectral distortion values are obtained for each of the various motion modes, one of the various motion modes is selected to be the motion mode that best matches the motion indicated by the collected motion data.

For time-domain classification, like the frequency domain, the movement data is collected from the sensors first. Then, various time-based classifications can be utilized in the hierarchical algorithm. For example, standard deviation of acceleration and/or angular rate data can be used. The Euclidean norm of the acceleration signal from a 3-axis accelerometer is described by the following expression:

$$AccNorm(i) = \sqrt{Acc_x(i)^2 + Acc_y(i)^2 + Acc_z(i)^2}$$

where $Acc_x$, $Acc_y$, and $Acc_z$ are the accelerations measured along the three orthogonal axes using the 3-axis accelerometer. An advantage of using the Euclidean norm of acceleration signal in the absolute difference method is that the user mode detection test may be conducted even when the device is in an arbitrary orientation. This is particularly useful for devices such as mobile handsets which can be carried by the user in arbitrary orientations.

The performance of the absolute difference method described above can also be enhanced by use of variance on the acceleration signal. A test to compare the absolute difference with a set of pre-determined threshold values can be combined with comparing the variance on the acceleration signal within the detection window with pre-determined threshold values for the variance. The variance of signal corresponds to the signal's noise power.

It should be apparent to persons skilled in the art that the Euclidean norm of acceleration signal and the variance on the acceleration signal may also be employed to process data in the frequency-domain method described before.

For a non-limiting illustrative example with 300 samples, mean and standard deviation are calculated as:

$$AccMean(i) = \frac{\sum_{n=1}^{n=i+299} AccNorm(i)}{\sum_{n=1}^{n=i+299} 1}$$

$$StdDev(i) = \sqrt{\frac{\sum_{i=n}^{i=n+299} AccNorm(i)^2 - AccMean(i)^2}{\sum_{i=n}^{i=n+299} 1}}$$

Standard deviation of acceleration data can be used to classify the location of the module on the body of the user since this parameter shows distinct demarcation in the computed value for each of the respective locations, such as, near a persons head (e.g., when he is talking on the phone where the navigation-module is embedded), near a person's waist (e.g., inside a holster attached to a person's belt), inside a trouser pocket, inside a shirt pocket, inside a backpack or a side-bag or a briefcase, etc.

Another example time-domain classifier may be the mean of norm of acceleration. This parameter is similar to standard deviation parameter described above:

$$Mean_{AccNorm}(i) = \frac{\sum_{n=1}^{n=i+299} AccNorm(i)}{\sum_{n=1}^{n=i+299} 1}$$

The number of zero crossings in the norm of raw acceleration data (after removing 'g', which represents gravitational acceleration) can also be used as a classifier for detecting the location of the module.

$$ZeroCrossings(i) = \sum_{i=n}^{i=n+299} \begin{cases} 1 & if\ AccNorm(i) = 0 \\ 0 & if\ AccNorm(i) \neq 0 \end{cases}$$

Figure 2:
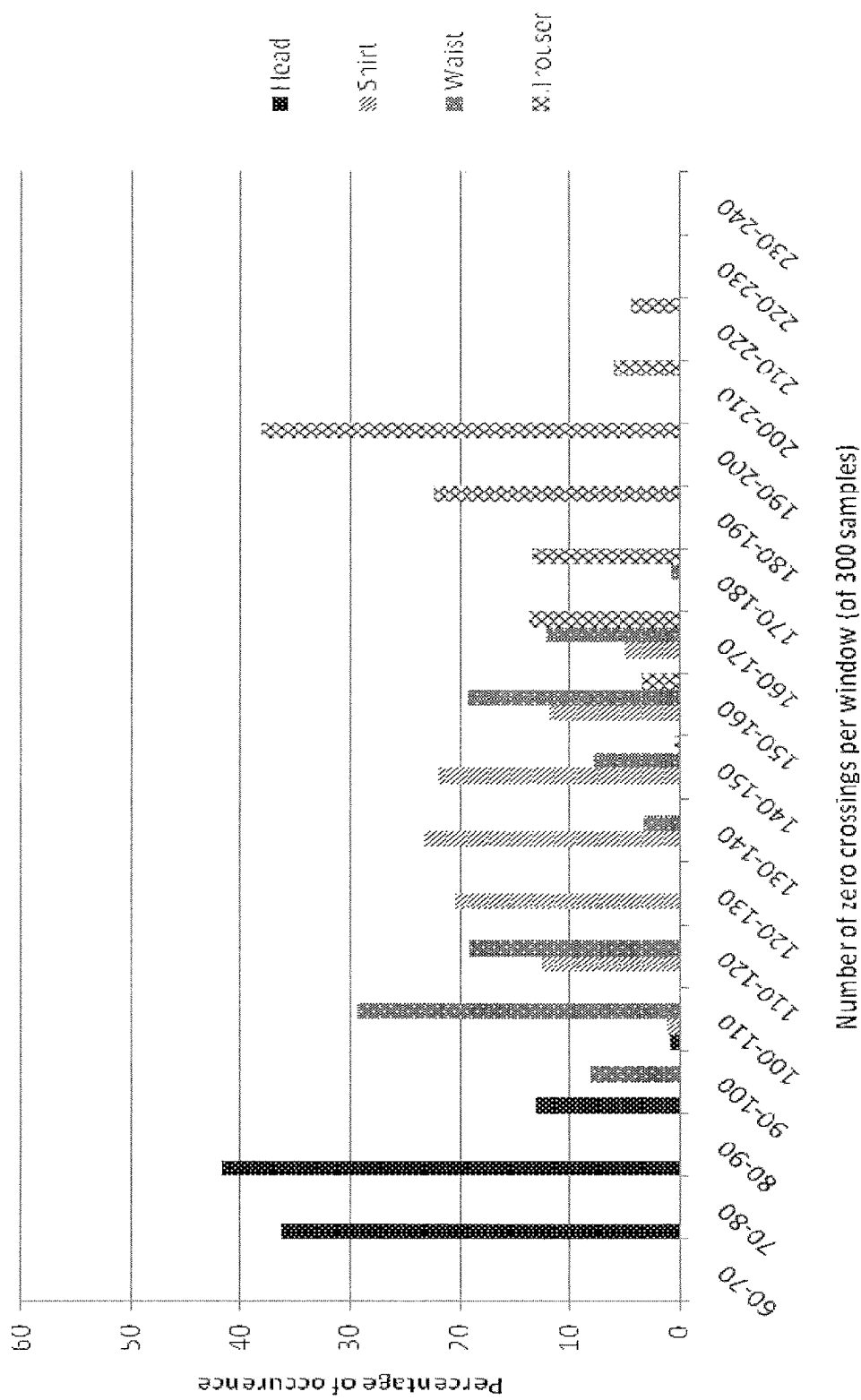
FIG. 2 is measured data illustrating zero-crossings in acceleration norm for a walking mode, according to an embodiment of the present invention.

Again, in this example this parameter is calculated over a sliding window of 300 samples, however the scope of the invention is not limited by the number of samples used. The zero-crossing parameter demonstrates definite patterns distinguishable for the different locations on body as shown in FIG. 2. In FIG. 2, the x axis indicates sample sub-windows, and the y-axis indicates percentage of occurrence of zero-crossings within each sub-window.

As shown in FIG. 2, when the device is fixed in a holster on waist or held firmly near the ear, the lateral (or sideways) acceleration is minimal. Hence the number of zero crossings for these two positions is smaller as compared to other locations on the body. As can be further seen from FIG. 2, when the device is in trouser pocket, it experiences a combination of forward acceleration variation due to pendulum motion of leg, lateral acceleration because of sideways motion of device in the trouser pocket and the periodic vertical acceleration associated with normal walking motion. Hence, the number of zero crossings for this location would be higher than other locations.

Another possible time-domain classifier may be the number of positive and negative peaks in the norm of raw acceleration data (after removing 'g', i.e. the gravitational acceleration parameter).

Figure 3:
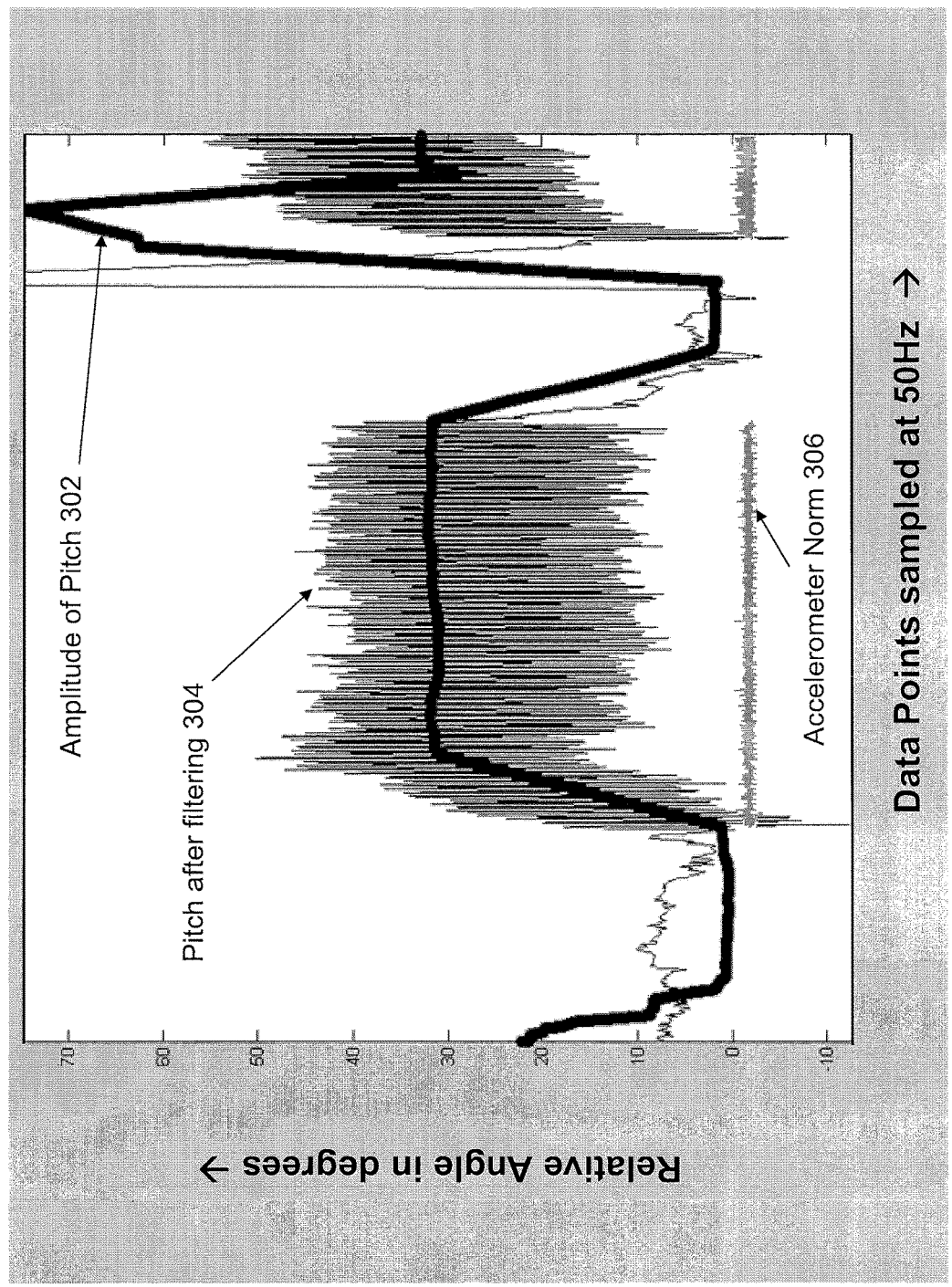
FIG. 3 is a graphical representation of accelerometer norm, pitch after filtering, and amplitude of pitch data, according to an embodiment of the present invention.

Yet another time-domain classifier may be amplitude of pitch variation. This classifier is based on the hypothesis that parts of the body/clothing, like a hand and trouser pocket shows a repetitive swinging motion while walking, fast walking or jogging and the amplitude of the swing is more for the hand than the trouser pocket. Both hand and trouser pocket swing are more than that of any other position on the human body, such as head, chest (where a shirt pocket is likely to be) etc. Thus the amplitude of pitch variation classifier is calculated by filtering the pitch values and taking the difference between the positive and the negative peaks. In embodiments, this difference is the angle of swing and is further averaged out over a sliding window of 300 (or other number of) samples to create the various thresholds for classifying module positions. FIG. 3 illustrates the amplitude of pitch variation curve 302 (the thick line) plotted along with accelerometer norm data 306 and post-filtering pitch data 304 in the same time scale. The y-axis of FIG. 3 is the relative angle of the detected position in degrees.

Persons skilled in the art will recognize, in view of the current discussion, that a combination of the time-domain classifiers may also be used in the hierarchical context detection algorithm.

Figure 4:
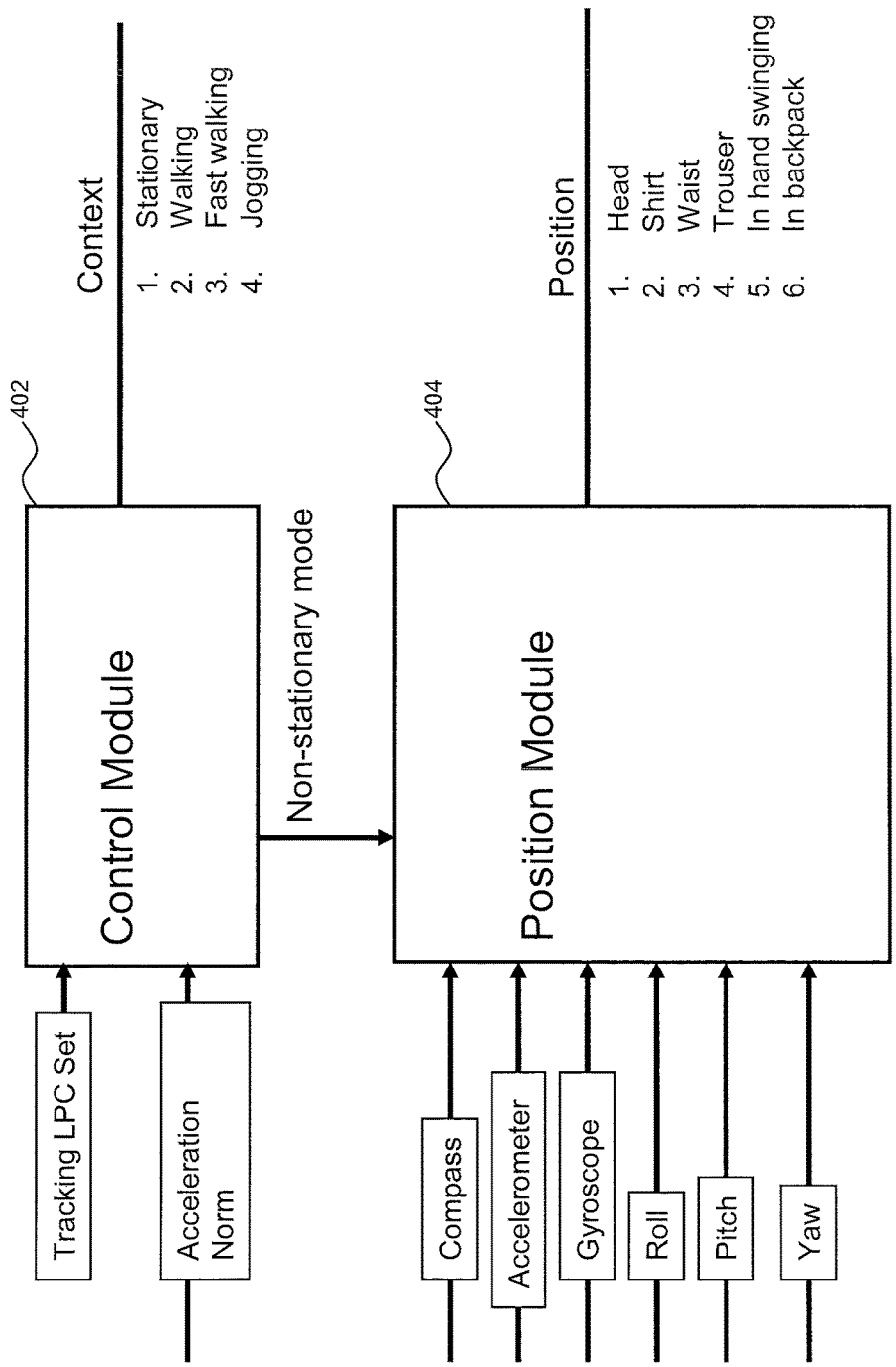
FIG. 4 is a block diagram of the hierarchical context detection concept, according to an embodiment of the present invention.
Figure 5:
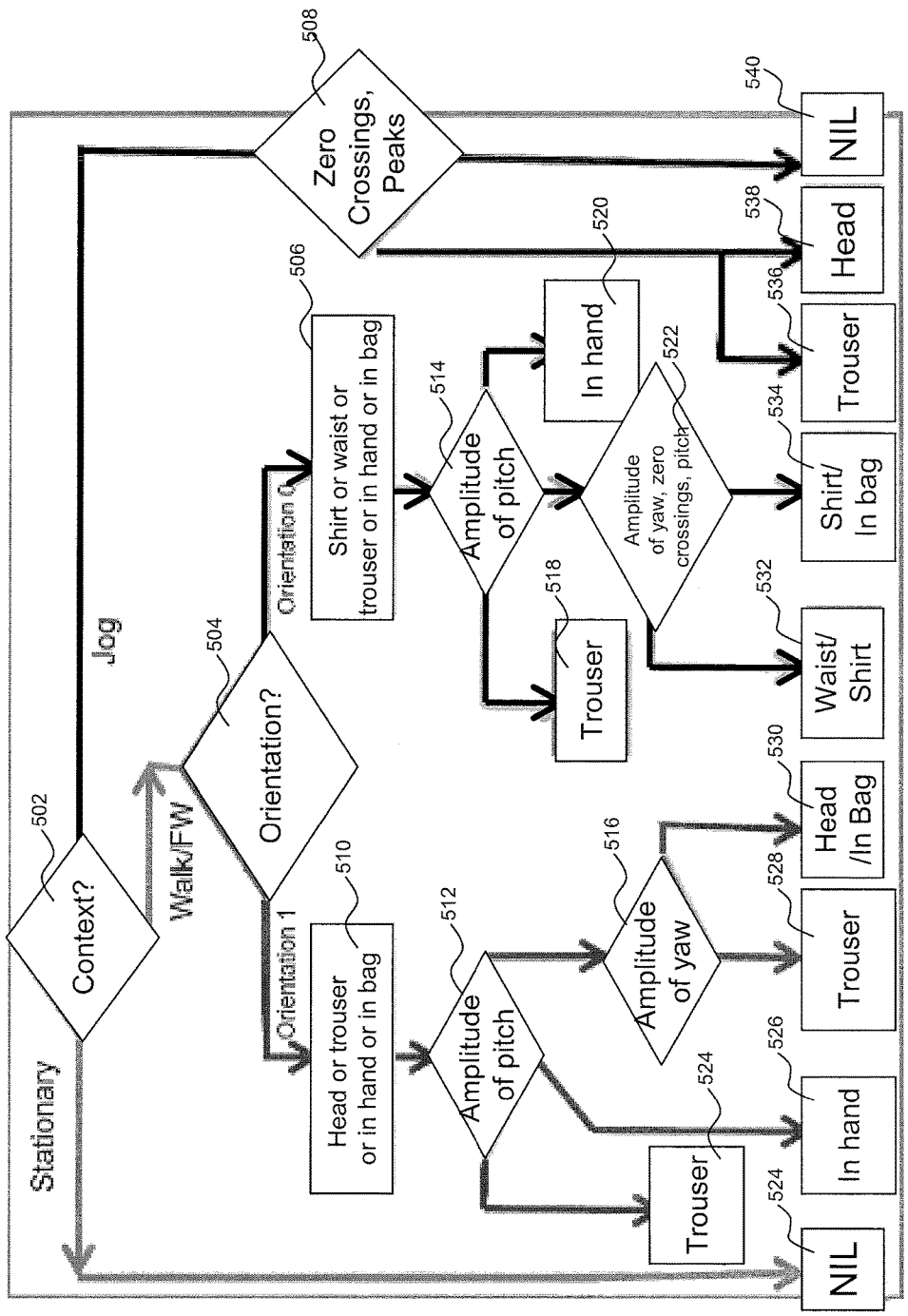
FIG. 5 is a flowchart showing an example method of determination of a navigation module location, according to an embodiment of the present invention.

An example hierarchical context detection algorithm to determine the location of the module on the body of person is described in FIGS. 4 and 5. In FIGS. 4 and 5, classification of the user mode of motion (context detection) is conducted first, and, next, for each mode, further classification of the module's location or position on the person's body is performed. It should be noted that the order in which the classification hierarchy is chosen determines the nature of the algorithm. Also, although in FIGS. 4 and 5, only two levels of classifications are discussed (motion mode detection and position detection on a person's body), the classification can potentially have more than two levels. For example, an additional level of classification may determine if the PND is outdoors, indoors, underground etc.

This algorithm may utilize LPC-LSF (as described in the context of frequency-domain classification) methods, followed by one or more of the above-discussed time-domain classifiers. A block diagram for an example embodiment of this algorithm is shown in FIG. 4. The algorithm may be executed in two main modules: a control module 402, and a position module 404 coupled to the control module 402. Control module 402 receives tracking LPC data for motion mode classification, and may be further assisted by a time-domain classifier, such as, acceleration norm data. The output of the control module is context information, such as whether the user carrying the PND is stationary, walking, fast walking, or jogging. Once a non-stationary mode is detected, the position module 404 analyzes data from the various sensors, such as a compass (magnetic sensor for orientation data), accelerometer, gyroscope, and roll, pitch and yaw indicative sensors. The output of the position module 404 is the precise location of the PND, i.e. whether it is near the head, in a shirt pocket, near the waist (possibly in a holster), in a trouser pocket, in a swinging hand (i.e. the user is moving), in a backpack etc.

An algorithmic flowchart for an example embodiment of detecting PND location on the body of the user is shown in FIG. 5. The user mode (walking, fast walking, jogging, or stationary) is the first decision (block 502) in this hierarchical context determination logic. If the user mode is walking or fast walking (FW), the orientation of device is used in next classification (block 504). When the device is oriented such that the direction perpendicular to plane of the device is parallel to walking direction of motion, then it is classified as orientation 0. This orientation is most commonly found when device is carried in shirt pocket, at the waist, or trouser pocket, or in hand, or in a bag (block 506). Orientation 1 is the case when the plane of the device is perpendicular to the walking direction of motion (most commonly found when the device is located close to head, but other possibilities include device in hand, or in trouser pocket, or in hand, or in a bag, as shown in block 510). Various time domain classifiers, such as, amplitude of pitch angle variation, number of zero crossings in norm of acceleration, number of peaks in acceleration data, and amplitude of yaw angle variation are utilized to determine the location of module on the body. However, these classifiers are all non-limiting examples, and can be replaced by other types of classifiers, because the algorithm's basic nature is independent of the classifiers. Similarly, more than just two orientations can be accommodated in the algorithm.

In the example shown in FIG. 5, if a stationary motion mode is detected in block 502, the PND location is determined to be "NIL" (block 524). If a jogging mode is determined in block 502, a further zero crossing, peaks decision step may be executed (block 508), and the location of the PND is determined to be in the trouser (block 536), near the head (i.e., a head-mounted component device, block 538), or "NIL" (block 540).

From block 506, further amplitude of pitch analysis may be performed in block 514 to determine whether the PND is in the trouser pocket (block 518), in hand (block 520), or the location is still uncertain. In the uncertain case, a subsequent step is performed in block 522 to analyze amplitude of yaw, zero crossings, and/or pitch. From block 522, it can be determined whether the PND is at the waist or in the shirt pocket (block 532), or in a shirt pocket/in a bag (block 534).

From block 510, further amplitude of pitch analysis may be performed in block 512 to determine whether the PND is in the trouser pocket (block 524), in hand (block 526), or the location is still uncertain. In the uncertain case, a subsequent step is performed in block 516 to analyze amplitude of yaw. From block 516, it can be determined whether the PND is in the trouser (block 528), or in a near the head/in a bag (block 530).

Note that FIGS. 4 and 5 do not cover an exhaustive set of possibilities, but are presented here as illustrative examples only. The central idea of the hierarchical algorithm that position detection can be fine tuned to a high accuracy level by contextually drilling down sensor data is not limited by the specific examples and the sequence of the operations.

Figure 6A:
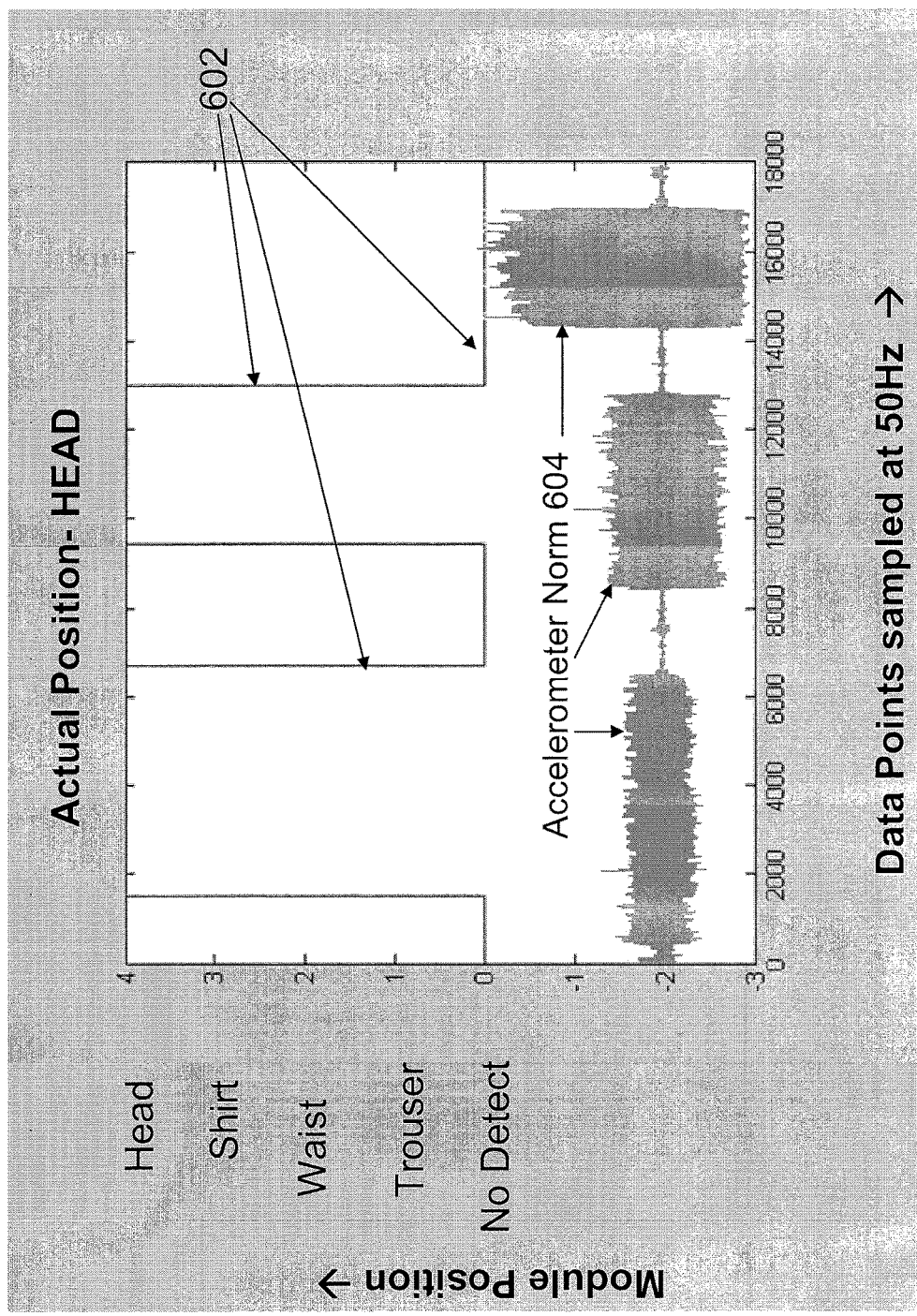
FIGS. 6A-C show results of module location determination algorithm, according to an embodiment of the present invention.
Figure 6B:
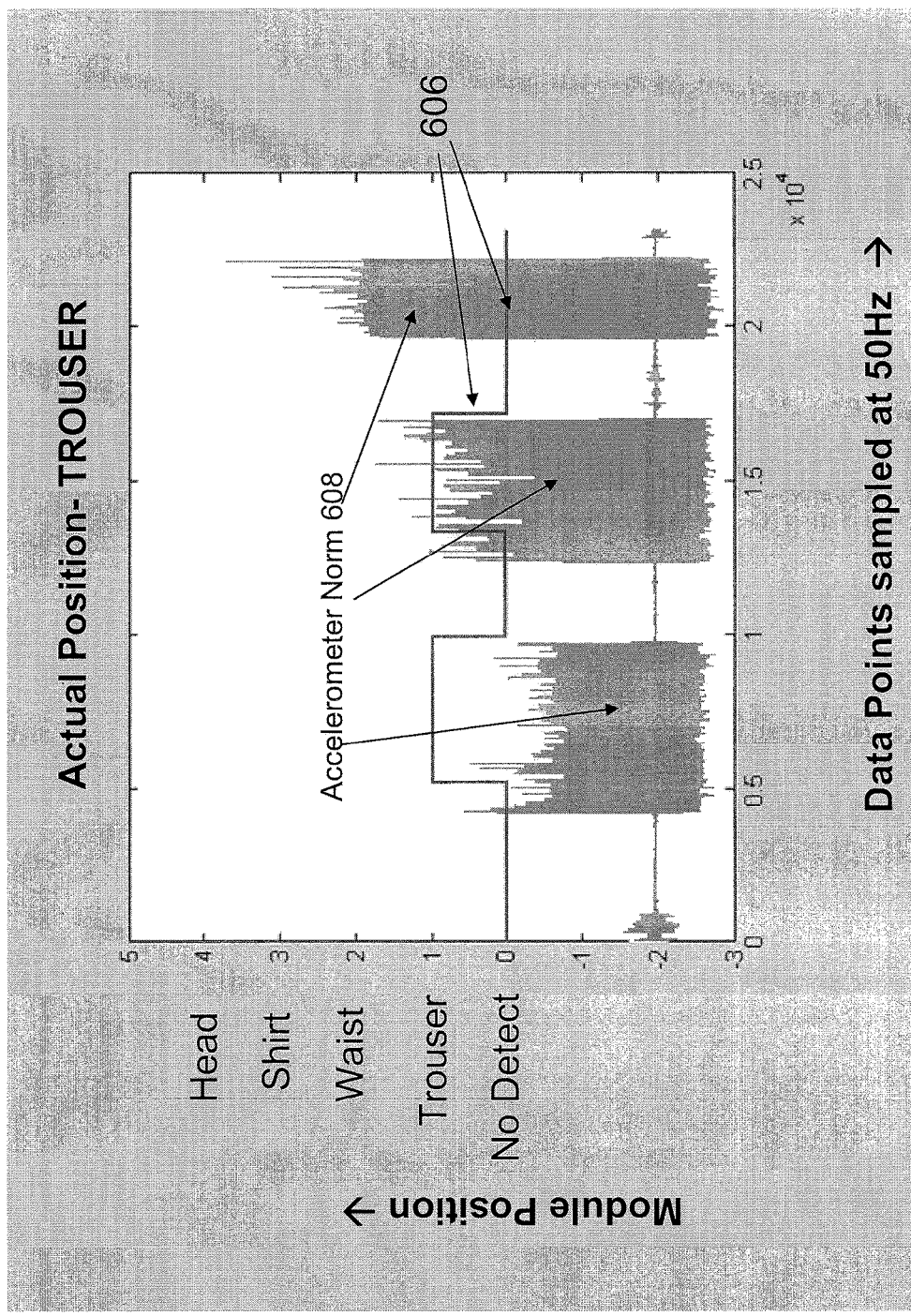
Figure 6C:
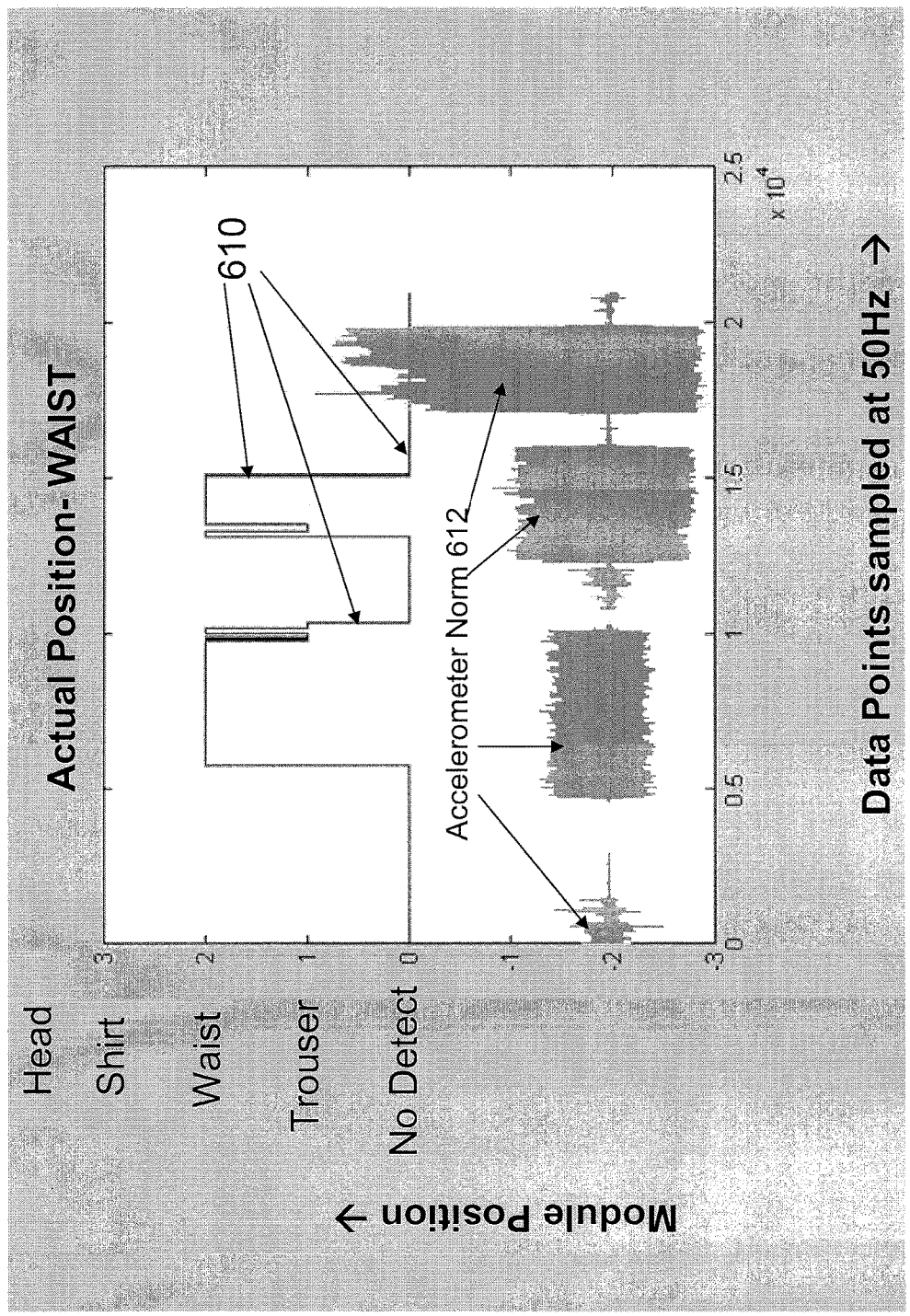

To prove the efficacy of one example embodiment of a hierarchical algorithm according to the invention, test data was collected for a plurality of users with different height and weight. FIGS. 6A-C show the results of module location determination logic used in the hierarchical algorithm. In each of the figures, the Euclidean norm of acceleration (along a certain axis of the accelerometer, e.g., the z-axis) is plotted on the same time axis for comparing the user mode for the test. For example, in FIG. 6A, the accelerometer noun data is shown as element 604, and the module location determination logic output is shown as the solid plot 602. The logic has arbitrary levels associated with various physical positions on the person's body, such as, level 1 indicates the PND is in the trouser pocket, level 2 indicates that the PND is at the waist (in a holster), level 3 indicates that the PND is in the shirt pocket, and level 4 indicates that the PND is near the person's head, i.e. the person is probably talking using the device containing the navigation module. Level 0 usually indicates that no signal is detected. Note that any arbitrary number of levels may be created if additional possible locations on the person's body are identified as the location where the PND is carried. Sampling data points at a non-limiting arbitrary sampling rate of 50 Hz, the algorithm can predict with a certain accuracy that the actual position of the PND was near the person's head.

In a similar manner, in FIGS. 6B, and 6C respectively, the logic results are plotted as solid plots 606 and 610, respectively. The corresponding accelerometer norm data are plots 608 and 612, respectively. In FIG. 6B, the location of the PND was determined to be in the trouser pocket, while in FIG. 6C, the location of the PND was determined to be in the waist holster.

Tables 1-3 show the results of one example embodiment of the hierarchical algorithm plotted in a 'confusion matrix' format, which is a quantitative representation of the confidence level with which the location of the PND is detected. A confidence level near or above 80% is typically considered good. In the Tables 1-2, orientation 1 and orientation 0 were predefined. Other orientations are possible too. When a location is not determined with an acceptable confidence level, further refinement of the hierarchical algorithm may be necessitated.

TABLE 1

Confusion Matrix for Orientation 1 between Near Head and Trouser pocket location

| Orientation = 1 | Near Head | Trouser Pocket |
|---|---|---|
| Near Head | 99.95 | 0.05 |
| Trouser Pocket | 0.03 | 99.97 |

TABLE 2

Confusion Matrix for Orientation 0 between shirt pocket, waist and Trouser pocket positions

| Orientation = 0 | Shirt Pocket | Waist | Trouser Pocket |
|---|---|---|---|
| Shirt Pocket | 31.11 | 59.78 | 9.11 |
| Waist | 5.21 | 79.58 | 15.41 |
| Trouser Pocket | 8.23 | 0 | 91.77 |

TABLE 3

Conditional confusion matrix for all cases

| Overall | Near Head | Shirt Pocket | Waist | Trouser Pocket |
|---|---|---|---|---|
| Near Head | 99.95 | 0 | 0 | 0.05 |
| Shirt Pocket | 0 | 31.11 | 59.78 | 9.11 |
| Waist | 0 | 5.21 | 79.58 | 15.41 |
| Trouser Pocket | 0.015 | 4.12 | 0 | 95.87 |

Though in the above discussion time-domain and frequency-domain classification have been shown separately, according to one aspect of the invention, the frequency-domain method and the time-domain methods may be used in a complementary manner to detect motion modes. For example, the time-domain method may be used to produce a first estimate, because the time-domain method needs only a small amount of data (e.g., a half-second worth of motion data) to produce an estimate. The frequency-domain method generally needs a larger amount of data (e.g., 2 to 3 seconds worth of motion data), but is typically more accurate over a longer span of time. In one embodiment, the results produced by the frequency-domain method are used to monitor the results produced by the time-domain method. In other words, the frequency-domain method may be used to check the motion mode classifications that result from using the time-domain method.

As described before, the approaches described herein can be used in any type of PND, including those also used in vehicles, as well as cell phones, iPhones, PDAs, wrist watches etc. with GPS functionality, handheld or laptop computers, and other type of device with built-in GPS functionality. Therefore, the configuration of the functions and the equipment can vary from implementation to implementation depending upon numerous factors, such as price constraints, performance requirements, technological improvements, or other circumstances.

Although the present invention has been particularly described with reference to the preferred embodiments thereof, it should be readily apparent to those of ordinary skill in the art that changes and modifications in the form and details may be made without departing from the spirit and scope of the invention. It is intended that the appended claims encompass such changes and modifications.

What is claimed is:

1. A method for using position information about a mobile device to enhance user experience, the method comprising:
    detecting, by a processor, a motion mode of the mobile device based on data collected from one or more sensors coupled to the mobile device;
    detecting, by the processor, a location of the mobile device on a user's body based on the detected motion mode and on the collected sensor data; and
    providing situational awareness information to the user based on the detected motion mode and the detected location of the mobile device,
    wherein detecting the motion mode of the mobile device includes:
        obtaining frequency-domain spectral information from the collected sensor data;
        comparing the spectral information from the collected sensor data to spectral information in two or more sets of training data, each set of training data in the two or more sets of training data corresponding to one of a plurality of particular motion modes; and
        determining, based on the comparison, the motion mode of the mobile device.

2. The method of claim 1, wherein detecting the location of the mobile device on the user's body comprises performing one or both of time-domain analysis and frequency-domain analysis of the data collected from the one or more sensors.

3. The method of claim 1, wherein detecting the location of the mobile device on the user's body comprises performing a time-domain classification using classifiers of data collected from the one or more sensors.

4. The method of claim 3, wherein the classifiers include one or more of standard deviation of acceleration, mean of norm of acceleration, zero crossings in the norm of acceleration, number of peaks in the norm of acceleration, amplitude of pitch variation, amplitude of yaw variation, and amplitude of roll variation.

5. The method of claim 1, wherein obtaining the frequency-domain spectral information comprises computing a set of linear predictor coefficients (LPC) for the collected sensor data.

6. The method of claim 5, wherein comparing the spectral information in the collected sensor data to spectral information in two or more sets of training data further comprises:
    converting the LPC to linear spectral frequencies (LSF) for the collected sensor data; and
    calculating a spectral distortion between the LSF for the collected sensor data and a LSF for each set of training data in the two or more sets of training data.

7. The method of claim 6, wherein determining, based on the comparison, the motion mode of the mobile device the plurality of motion modes comprises:
    identifying a particular motion mode whose corresponding set of training data has LSF that have a least amount of spectral distortion with the LSF of the collected sensor data.

8. The method of claim 1, wherein the plurality of particular motion modes includes two or more of: stationary, walking, fast walking, jogging, climbing up/down stairs, going up/down on an escalator, going up/down on an elevator, biking, driving, and riding in a vehicle.

9. The method of claim 1, wherein the detected location is used to select a dead-reckoning (DR) positioning algorithm.

10. The method of claim 1, wherein the plurality of particular motion modes includes at least one non-stationary motion mode.

11. The method of claim 1, wherein detecting the location of the mobile device on the user's body includes:
  determining whether an orientation of the mobile device is one of a first orientation and a different second orientation.

12. The method of claim 11, wherein the detected motion mode is walking or fast walking.

13. The method of claim 11, wherein detecting the location of the mobile device on the user's body further includes:
  determining whether the mobile device is located near the user's head, in the user's hand, or in a bag carried by the user in response to determining that the orientation of the mobile device is the first orientation.

14. The method of claim 13, wherein the detected motion mode is jogging or running.

15. The method of claim 11, wherein detecting the location of the mobile device on the user's body further includes:
  determining whether the mobile device is located in the user's trousers, near the user's waist, in the user's hand, in the user's shirt, or in a bag carried by the user in response to determining that the orientation of the mobile device is the second orientation.

16. The method of claim 1, wherein detecting the location of the mobile device on the user's body includes:
  determining a head or trouser location of the mobile device.

17. The method of claim 1, wherein the sensors comprise an inertial measurement unit (IMU).

\* \* \* \* \*